United States Patent
Kasahara et al.

(10) Patent No.: US 11,547,102 B2
(45) Date of Patent: Jan. 10, 2023

(54) METHOD FOR SCREENING SALTINESS ENHANCER USING SALTINESS RECEPTOR

(71) Applicants: NISSIN FOODS HOLDINGS CO., LTD., Osaka (JP); THE UNIVERSITY OF TOKYO, Tokyo (JP)

(72) Inventors: Yoichi Kasahara, Osaka (JP); Tomiko Asakura, Tokyo (JP); Keiko Abe, Tokyo (JP); Yoshiro Ishimaru, Tokyo (JP); Masataka Narukawa, Tokyo (JP)

(73) Assignees: NISSIN FOODS HOLDINGS CO., LTD., Osaka (JP); THE UNIVERSITY OF TOKYO, Tokyo (JP)

( * ) Notice: Subject to any disclaimer, the term of this patent is extended or adjusted under 35 U.S.C. 154(b) by 305 days.

(21) Appl. No.: 16/958,488

(22) PCT Filed: Dec. 27, 2018

(86) PCT No.: PCT/JP2018/048305
§ 371 (c)(1),
(2) Date: Jun. 26, 2020

(87) PCT Pub. No.: WO2019/131936
PCT Pub. Date: Jul. 4, 2019

(65) Prior Publication Data
US 2021/0360907 A1 Nov. 25, 2021

(30) Foreign Application Priority Data
Dec. 28, 2017 (JP) .............................. JP2017-254219

(51) Int. Cl.
*A01K 67/027* (2006.01)
*A23K 20/10* (2016.01)
*G01N 33/68* (2006.01)

(52) U.S. Cl.
CPC .......... *A01K 67/0276* (2013.01); *A23K 20/10* (2016.05); *G01N 33/6872* (2013.01); *A01K 2217/075* (2013.01); *A01K 2227/105* (2013.01); *A01K 2267/03* (2013.01)

(58) Field of Classification Search
CPC ..................................................... A23L 27/88
See application file for complete search history.

(56) References Cited

U.S. PATENT DOCUMENTS

| | | |
|---|---|---|
| 9,222,944 B2 | 12/2015 | Ishiwatari et al. |
| 10,175,228 B2 | 1/2019 | Maekawa et al. |
| 2012/0028263 A1 | 2/2012 | Ishiwatari et al. |
| 2018/0095071 A1 | 4/2018 | Maekawa et al. |

FOREIGN PATENT DOCUMENTS

| | | |
|---|---|---|
| JP | 2012-154661 | 8/2012 |
| JP | 2017-135996 | 8/2017 |
| JP | 2018-14999 | 2/2018 |
| WO | 2007/146120 | 12/2007 |
| WO | 2011/040475 | 4/2011 |

OTHER PUBLICATIONS

Mancina et al., The MBOAT7-TMC4 Variant rs641738 Increases Risk of Nonalcoholic Fatty Liver Disease in Individuals of European Descent. Gastroenterology, (20160500) vol. 150, No. 5, pp. 1219-1230.e6 (Year: 2016).*
International Search Report dated Mar. 26, 2019 in International (PCT) Application No. PCT/JP2018/048305.
Marios Chatzigeorgiou et al., "*tmc*-1 encodes a sodium-sensitive channel required for salt chemosensation in *C. elegans*", Nature, Feb. 7, 2013, vol. 494, pp. 95-99.
Kiyoto Kurima et al., "Characterization of the transmembrane channel-like (*TMC*) gene family: functional clues from hearing loss and epidermodysplasia verruciformis", Genomics, 2003, vol. 82, pp. 300-308.
Jayaram Chandrashekar et al., "The cells and peripheral representation of sodium taste in mice", Nature, 2010, vol. 464, pp. 297-301.
Vijay Lyall et al., "The mammalian amiloride-insensitive non-specific salt taste receptor is a vanilloid receptor-1 variant", J. Physiol., 2004, vol. 558.1, pp. 147-159.
Yuki Oka et al., "High salt recruits aversive taste pathways", Nature, 2013, vol. 494, pp. 472-475.
Extended European Search Report dated Aug. 12, 2021, for the corresponding European Application No. 18894127.2.
Schindler et al., "Discovery of Salt Taste Enhancing Arginyl Dipeptides in Protein Digests and Fermented Fish Sauces by Means of a Sensomics Approach", Journal of Agriculture and Food Chemistry, vol. 59, No. 23, 2011, pp. 12578-12588.

* cited by examiner

*Primary Examiner* — Qiuwen Mi
(74) *Attorney, Agent, or Firm* — Wenderoth, Lind & Ponack, L.L.P.

(57) ABSTRACT

A method for screening an active ingredient of a saltiness enhancer, the screening method including the following steps: (i) a step for determining whether a test substance is a compound capable of promoting functional expression of the TMC4 gene or TMC4 protein; and (ii) a step for selecting, as an active ingredient of a saltiness enhancer, a test substance that has been determined in step (i) to be a compound capable of promoting functional expression of the TMC4 gene or TMC4 protein.

1 Claim, 5 Drawing Sheets

METHOD FOR SCREENING SALTINESS ENHANCER USING SALTINESS RECEPTOR

TECHNICAL FIELD

The present invention relates to mainly a method for screening for a salty taste enhancer, a salty taste enhancer, and a model animal having palatability to a high salt concentration.

BACKGROUND ART

Gustatory sense is one of five senses, and the sense is received by taste buds distributed on the intraoral epithelium. The stimulus is transmitted through the chorda tympani nerve and glossopharyngeal nerve to the taste area of the brain to be recognized.

As principal types of the gustatory sense, five basic tastes (sweet taste, umami (savory), bitter taste, sour taste and salty taste) are known. As for sweet taste, umami and bitter taste, G protein-coupled receptor (GPCR) present in type II taste cells is known as the receptor. As for sour taste, it has been found through an experiment using diphtheria toxin that a sour taste receptor is present in type III cells, but a principal receptor has not been found yet.

Salty taste is a taste of salt (the principal ingredient is sodium chloride (NaCl)), and is a sense felt when NaCl is dissolved in the oral cavity and $Na^+$ ion and $Cl^-$ ion thus ionized are sensed with the tongue.

As a molecule playing a role as a salty taste receptor molecule, as for a cation, it has been reported that epithelial sodium channel (ENaC) $\alpha\beta\gamma$, that is, an amiloride sensitive (AS) epithelial $Na^+$ channel, expresses, in the form of a heterotrimer, in type I cells of fungiform papillae present in a front portion of the tongue to receive low concentration salt (palatable) (Non Patent Literature 1).

Besides, as a receptor molecule of a high concentration salt (repellent), TRPV1t, that is, a splicing valiant of transient receptor potential cation channel subfamily V member 1 (TRPV1), is described as a candidate (Non Patent Literature 2).

Besides, there has been no report on a molecule receiving the anion of $Cl^-$.

Since ENaC $\alpha\beta\gamma$ expresses in type I cells of fungiform papillae, it has been considered that salty taste is received by type I taste cells. Recently, however, there has been a theory that salty taste is received in conjugation of type II cells and type III cells, and discussion on which cells receive salty taste has not been concluded yet (Non Patent Literature 3).

NaCl is a significant nutrient ingredient for living things, and plays, in a human body, various roles in homeostasis of moisture balance and adjustment of pH, osmotic pressure and nerve conductance. It is considered, however, that excessive ingestion of $Na^+$ is deeply linked to a risk of stomach cancer or hypertension, and it is desired to reduce the amount of salt ingested from food. When NaCl contained in food is simply reduced for this purpose, the taste of the food becomes too plain to get a sense of satisfaction. Therefore, there is a demand for development of a salty taste enhancer capable of making salty taste felt stronger without changing a salt concentration by searching a salty taste receptor and activating the receptor.

CITATION LIST

Non Patent Literature

Non Patent Literature 1: Chandrashekar et al., Nature. 2010 Mar. 11; 464 (7286): 297-301

Non Patent Literature 2: Lyall et al., J Physiol. 2004 Jul. 1; 558 (Pt 1): 147-159

Non Patent Literature 3: Oka et al., Nature. 2013 Feb. 28; 494 (7438): 472-475

SUMMARY OF INVENTION

Technical Problem

An object of the present invention is to provide a method for screening for a salty taste enhancer, a salty taste enhancer, and a model animal having palatability to a high salt concentration.

Solution to Problem

The present inventors made earnest studies to solve the above-described problem, resulting in finding that TMC4 protein, whose function has been unknown, is involved in reception of salty taste. The present invention was accomplished through modifications made based on the finding.

Specifically, the present invention provides the following aspects of the invention.

Item 1. A method for screening for an active ingredient of a salty taste enhancer, comprising the steps of:

(i) determining whether or not a test substance is a compound capable of upregulating functional expression of TMC4 gene or TMC4 protein; and (ii) selecting a test substance determined in step (i) to be the compound capable of upregulating functional expression of TMC4 gene or TMC4 protein, as the active ingredient of a salty taste enhancer.

Item 2. A salty taste enhancer, comprising a compound capable of upregulating functional expression of TMC4 gene or TMC4 protein.

Item 3. The salty taste enhancer according to item 2, wherein the compound is an ingredient derived from a food.

Item 4. A model animal having palatability to a high salt concentration, wherein the model animal is a non-human animal having knocked-out TMC4 gene.

Item 5. The model animal according to item 4, wherein the model animal is a mouse.

Advantageous Effects of Invention

The present invention provides a novel method for screening for a salty taste enhancer, and a salty taste enhancer.

Owing to the salty taste enhancer provided by the present invention, salty taste can be strongly felt with a salt concentration suppressed, and thus, adequate satisfaction can be felt in eating and drinking. Besides, a screening method and a model animal of the present invention are useful as tools for research and development, and can make contribution to further development of food industry and health science.

DESCRIPTION OF EMBODIMENTS

TMC4 Gene and TMC4 Protein

TMC (transmembrane channel like) 4 gene is a known gene, and TMC4 protein is a known protein. TMC4 protein is one of TMC proteins. A TMC protein is a membrane protein having an eight-transmembrane domain, and including the N-terminal and C-terminal in a cell. The TMC protein has a common region designated as a TMC motif between TM5 and TM6. In a mammal, the TMC proteins belong to the anoctamin family in view of their sequences.

Nucleotide sequences of cDNAs of TMC4 genes and amino acid sequences of TMC4 proteins of, for example, human (*Homo sapiens*) and a mouse (*Mus musculus*) are registered in GenBank provided by National Center for Biotechnology Information (NCBI), USA with the following accession numbers (it should be understood that the latest revision is referred to when a plurality of revisions are registered):

Human TMC4 gene: NM_001145303 (NM_001145303.2), NM_144686 (NM_144686.3), BC025323 (BC025323.1)

Human TMC4 protein: NP_001138775 (NP_001138775.2), NP_653287 (NP_653287.2)

Mouse TMC4 gene: NM_181820 (NM_181820.2)

Mouse TMC4 protein: NP_861541 (NP_861541.2)

Salty Taste Enhancer

A salty taste enhancer of the present invention contains a compound capable of upregulating functional expression of the TMC4 gene or the TMC4 protein.

The term "salty taste enhancer" in the present invention refers to a substance that does not present salty taste by itself but has an effect of enhancing salty taste of sodium chloride (NaCl, salt) simultaneously present.

As the compound capable of upregulating the functional expression of the TMC4 gene or the TMC4 protein, any of various compounds can be used as long as the functional expression of the TMC4 gene or the TMC4 protein can be upregulated. Examples of the compound capable of upregulating the functional expression of the TMC4 gene or the TMC4 protein include, but are not limited to, an activator specific to the TMC4 protein, and a nucleic acid capable of upregulating the expression of the TMC4 gene.

The term "upregulate the functional expression of the TMC4 gene or the TMC4 protein" herein refers to all the aspects in which the functional expression of the TMC4 gene or the TMC4 protein is upregulated, and examples include, but are not limited to, activation of the function of the TMC4 protein, and upregulation of the expression of the TMC4 protein (such as upregulation of transcription of the TMC4 gene, or upregulation of translation of the TMC4 protein). An example of the aspect in which the function of the TMC4 protein is activated includes upregulation of Cl$^-$ ion flux into cells via the TMC4 protein regarded as a Cl$^-$ ion channel.

An agonist of the TMC4 protein is one of preferable aspects of the present invention.

The term "capable of upregulating the expression of the TMC4 gene" can be, for example, but not limited to, an aspect in which the expression level of the TMC4 protein is upregulated through transcriptional promotion of the TMC4 gene, translational promotion into the TMC4 protein, or the like (namely, an aspect in which the expression level of the TMC4 protein is increased).

The compound capable of upregulating the functional expression of the TMC4 gene or the TMC4 protein can be obtained, for example, by a screening method described later.

The compound capable of upregulating the functional expression of the TMC4 protein can used singly, or in combinations of two or more.

The salty taste enhancer of the present invention can be provided, for example, in the form of food (a food composition). Alternatively, it can be provided in the form of a food-derived component, such as a metabolite, or a chemically or physically decomposed product of food (such as a sugar, an amino acid, a peptide, a lipid, or a compound of any of these).

When the salty taste enhancer of the present invention is provided in the form of a food composition, it can be prepared in a form in which the compound capable of upregulating the functional expression of the TMC4 gene or the TMC4 protein corresponding to an active ingredient is added to food or drink. The form of the food or drink is not especially limited, and examples include a seasoning such as soy sauce, miso, sauce or ketchup, hydrolyzed animal or vegetable protein (HAP, HVP), a seasoning principally containing a yeast extract, an amino acid, a peptide or the like, flavoring food used for seasoning of food such as Japanese instant bouillon, Japanese noodle soup base, Tare sauce, roux or dressing, processed grain products such as noodles, bread and snacks, processed meat and fish products such as ham, sausage and a fish paste product, a soup, pickles, and ready-to-eat dishes. Besides, the food or drink embraces instant food products that can be cooked merely by adding hot water or water (such as a powdered or liquid soup for instant noodles, instant consomme, potage and Chinese soups, miso soup, Japanese clear soup, and soup-type instant noodles).

Alternatively, the salty taste enhancer can be provided in the form of a substance generated during metabolism of the food composition in a living body (such as a sugar, an amino acid, a peptide or a lipid).

The content of the compound capable of upregulating the functional expression of the TMC4 gene or the TMC4 protein used as the active ingredient of the salty taste enhancer of the present invention is generally in a range of 0.01 to 100% by weight.

The salty taste enhancer of the present invention can be used in an abundance ratio or a content ratio of 1 to 15 parts by weight with respect to 100 parts by weight of sodium chloride.

The present invention also embraces the following aspects:

use, as a salty taste enhancer, of a compound capable of upregulating the functional expression of the TMC4 gene or the TMC4 protein;

a compound, for use as a salty taste enhancer, capable of upregulating the functional expression of the TMC4 gene or the TMC4 protein; and use of a compound, for producing a salty taste enhancer, capable of upregulating the functional expression of the TMC4 gene or the TMC4 protein.

Screening Method

A screening method of the present invention includes the following steps of:

(i) determining whether or not a test substance is a compound capable of upregulating the functional expression of the TMC4 gene or the TMC4 protein; and (ii) selecting a test substance determined in step (i) to be the compound capable of upregulating the functional expression of the TMC4 gene or the TMC4 protein, as the active ingredient of a salty taste enhancer.

In step (i), it is determined whether or not a test substance to be screened is a compound capable of upregulating the functional expression of the TMC4 gene or the TMC4 protein.

The test substance is not especially limited as long as it is a compound that can be a candidate compound of the active ingredient of the salty taste enhancer. The test substance may be either a natural compound (such as a biological material) or a synthesized compound. The test substance is preferably a compound derived from food. Specific examples of the test substance include a low molecular weight compound, a protein such as an antibody, a nucleic acid (such as siRNA, shRNA, dsRNA or miRNA), a sugar chain, and a complex carbohydrate.

Means for determining whether or not the test substance is a compound capable of upregulating the functional expression of the TMC4 gene or the TMC4 protein can be appropriately selected from all means known to those skilled in the art and developed in the future, as long as the purpose is achieved, in accordance with the test substance corresponding to a target of the determination and the functional expression of the TMC4 gene or the TMC4 protein to be determined in upregulation.

For example, it is possible to employ a method in which the test substance is caused to act on a cultured cell in which the TMC4 protein is expressed by introducing the TMC4 gene into cells (such as HEK293T), on an amphibian oocyte (such as a *Xenopus* oocyte), or on an artificial lipid membrane into which the TMC4 protein is incorporated, and a response is observed.

Specific examples of a method for observing a response include a patch clamp method (such as a cell-attach method, an inside-out method or a whole-cell method), measurement of whole cell current, a radiolabeled ion flux assay, and a fluorescence assay using a voltage sensitive dye and an ion sensitive dye. Specific methods for practicing these methods are well known to those skilled in the art.

In the patch clamp method and the measurement of whole cell current, change in ion influx into cells expressing the TMC4 protein can be detected as a change in a current or a voltage.

In the radiolabeled ion flux assay, change in ion influx into cells expressing the TMC4 protein can be detected by using radioisotope ions. In the fluorescence assay using a voltage sensitive dye and an ion sensitive dye, ion influx into cells expressing the TMC4 protein can be detected as a change in fluorescence intensity. The change in fluorescence intensity can be measured using, for example, a plate reader.

In these methods, a compound upregulating the influx of $Cl^-$ ions into cells via the TMC4 protein can be selected as the compound capable of upregulating the functional expression of the TMC4 protein.

Alternatively, it can be determined whether or not a test substance is a compound capable of upregulating the functional expression of the TMC4 protein also by structure-activity relationship simulation using a structural model based on the amino acid sequence of the TMC4 protein. For example, a three-dimensional structural model of the TMC4 protein is constructed, so that a ligand activating a pore region can be screened on the basis of docking simulation with the three-dimensional structural model.

For example, a compound having a high concordance rate when docked with a three-dimensional structure region site affecting molecular activity of the TMC4 protein can be selected as the compound capable of upregulating the functional expression of the TMC4 protein. Specific examples include:

(1) a method in which a three-dimensional structure region site affecting the molecular activity is presumed based on alignment between a protein having similar properties to those of the TMC4 protein and having a known three-dimensional structure and the TMC4 protein, and a ligand matching the structure is screened by the docking simulation with the three-dimensional structure region site; and (2) a method, employed when the compound (ligand) activating the protein having similar properties to those of the TMC4 protein and having a known three-dimensional structure is known, in which the docking simulation is performed based on the three-dimensional structure of the ligand to presume a region of the ligand acting on the structural region of the TMC4 protein, and a ligand structure more activating the TMC4 protein is screened based on the three-dimensional structure of a docking site.

In this step, a known salty taste enhancer such as arginine or a salt thereof (such as arginine hydrochloride) can be used as a control to select a test substance having a higher degree of upregulation of the functional expression of the TMC4 gene or the TMC4 protein than the control.

Subsequently, the active ingredient of the salty taste enhancer is selected in step (ii).

Model Animal

A non-human animal used as a model animal having palatability to a high salt concentration in the present invention is a non-human animal having knocked-out TMC4 gene.

The non-human animal can be an animal of any species as long as it is not a human and can be used as an experimental animal, and is preferably a rodent, and more preferably a mouse.

Herein, the term "knocked-out TMC4 gene" refers to a state where an expression product of the TMC4 gene is not expressed at all, or even if expressed, the expression product cannot exhibit a function that a normal product of the TMC4 gene has and is lack of the function of the TMC4 gene due to modification or the like of the nucleotide sequence of the TMC4 gene described above.

The non-human animal used in the present invention is not especially limited in a specific aspect of the lack of the function of the TMC4 gene as long as the TMC4 gene is knocked out therein, and examples include an aspect in which at least part of the TMC4 gene is modified, and an aspect in which a promoter of the TMC4 gene is inactivated.

Herein, the term "at least part of the TMC4 gene is modified" refers to that at least part of the nucleotide sequence of the TMC4 gene is modified to have deletion, substitution or addition. To knock out the TMC4 gene, a combination of one, two or more of deletion, substitution and addition may be employed for causing mutation in the TMC4 gene.

Besides, the term "to delete" at least part of the nucleotide sequence of the TMC4 gene herein refers to modification caused by deleting part or the whole of the TMC4 gene so that an expression product of the TMC4 gene cannot exhibit the function as the TMC4 protein. The term "to substitute" at least part of the nucleotide sequence of the TMC4 gene herein refers to modification caused by substituting part or the whole of the TMC4 gene with another sequence not related to the TMC4 gene so that an expression product of the TMC4 gene cannot exhibit the function as the TMC4 protein. Furthermore, the term "to add" to at least part of the nucleotide sequence of the TMC4 gene herein refers to modification caused by adding, to the TMC4 gene, a sequence different from the TMC4 gene so that an expression product of the TMC4 gene cannot exhibit the function as the TMC4 protein.

The non-human animal having knocked-out TMC4 gene used in the present invention may be a heterozygous knockout animal in which either one of alleles in the TMC4 gene is knocked out, or may be a homozygous knockout animal in which functions of both the alleles are knocked out.

The non-human animal used in the present invention may be either a female or a male.

The non-human animal having knocked-out TMC4 gene can be produced by a known method. Examples of the method include, but are not limited to, genome editing technologies such as TALEN method and CRISPR/Cas9 method, and gene disruption technology by a homologous recombination method.

The non-human animal having knocked-out TMC4 gene has palatability to a high salt concentration as verified in Examples described below, and hence can be used as a model animal having such palatability.

The present invention also embraces the following aspects:

use of a non-human animal having knocked-out TMC4 gene as a model animal having palatability to a high salt concentration; and a non-human animal having knocked-out TMC4 gene for use as a model animal having palatability to a high salt concentration.

EXAMPLES

The present invention will now be described in more detail with reference to Examples. It is noted that these Examples do not limit the present invention.

[Example 1] Expression Pattern of TMC4

It was confirmed by in situ hybridization that TMC4 is locally present in intraoral tissues having taste buds (circumvallate papillae, foliate papillae and fungiform papillae).
<Method>
In Situ Hybridization Seven-week-old or older wild-type C57BL/6J (B6) male mice (purchased from Clea Japan, Inc.) were used. The mice were euthanized by cervical dislocation, and epitheliums around the papillae were then harvested from the tongues to be embedded in Cryomold No. 1 (Sakura Finetek Japan Co., Ltd.) with O.C.T. Compound (Sakura Finetek Japan Co., Ltd.), and the resultant was frozen using liquid nitrogen. Each frozen block was sliced into a thickness of 7 μm, and the resultant was attached to MAS-coated Slide Glass (Matsunami Glass Ind., Ltd.).

A digoxigenin-labeled antisense RNA was synthesized through an in vitro transcription reaction with T3 RNA Polymerase (Stratagene Corporation) using DIG RNA labeling mix (Roche Diagnostics K.K.). Thereafter, the resultant was treated with an alkaline sizing buffer (42 mM NaHCO$_3$, 63 mM Na$_2$CO$_3$) at 65° C. for 55 minutes to fragment the antisense RNA to a size of about 150 bases by hydrolysis, and thus, an RNA probe was obtained.

Each of the thus obtained frozen sections of circumvallate, foliate or fungiform papillae was dried by blowing with cold air for 15 minutes, then immobilized in a 4% PFA/PBS solution for 15 minutes, and washed with a 0.1% DEPC/PBS solution twice. In order to make the probe easily penetrate, the resultant was treated with a TBS solution containing Proteinase K (1 μg/ml, Invitrogen Corporation) for 5 minutes, and further washed with a 0.1% DEPC/PBS solution. Then, the section was immersed in DEPC water containing 1.175 triethanolamine and 0.25% acetic anhydride to perform acetylation. The resultant was washed with DEPC water, then dried to an extent where a peripheral portion of the section was dried, and immersed in a prehybridization solution (50% formamide, 5×SSC, fish sperm DNA (40 μg/ml)) to be prehybridized at 58° C. for 2 hours in a humid box. Thereafter, the resultant was treated with a hybridization solution (50% formamide, 5×SSC, 5×Denhardt's solution, yeast RNA (0.25 mg/ml), 1 mM DTT, fish sperm DNA (0.5 mg/ml)) at 85° C. for 3 minutes. The resultant was dropped on the section, covered with a Parafilm, and hybridized at 58° C. overnight. After the hybridization, the resultant was washed with 5×SSC at 58° C. for 5 minutes twice and with 0.2×SSC for 30 minutes twice. The resultant was washed with a TBS solution for 5 minutes, and immersed in a blocking solution (0.1% Blocking Reagent (Roche Diagnostic K.K.)/TBS) at room temperature for about 1 hour to perform blocking. Thereafter, an antigen antibody reaction was performed at room temperature for 1 hour in a blocking solution containing an alkaline phosphatase-labeled anti-digoxigenin antibody (0.1 μl/ml, Roche Diagnostic K.K.). The resultant was washed with a TBS solution for 15 minutes three times, and immersed in an alkaline phosphatase buffer (100 mM Tris-HCl (pH 9.5), 100 mM NaCl, 50 mM MgCl$_2$) for 5 minutes.

Thereafter, an NBT (nitro-blue tetrazolium)/BCIP (5-bromo-4-chloro-3-indolyl phosphatase p-toluidine salt) solution (Roche Diagnostics K.K.) was added thereto as a chromogenic substrate in a dropwise manner, followed by a chromogenic reaction at room temperature overnight. After the chromogenic reaction was stopped by washing with an alkaline phosphatase buffer for 5 minutes, the resultant was immersed in ultrapure water for 5 minutes. The resultant was dried, and covered with cover glass using Fluoromount (Sigma) to obtain a preparation. The preparation was observed with a microscope BX51 (Olympus Corporation), and an image thereof was obtained with a cooled CCD camera DP73 (Olympus Corporation).
<Results>

Figure 1:
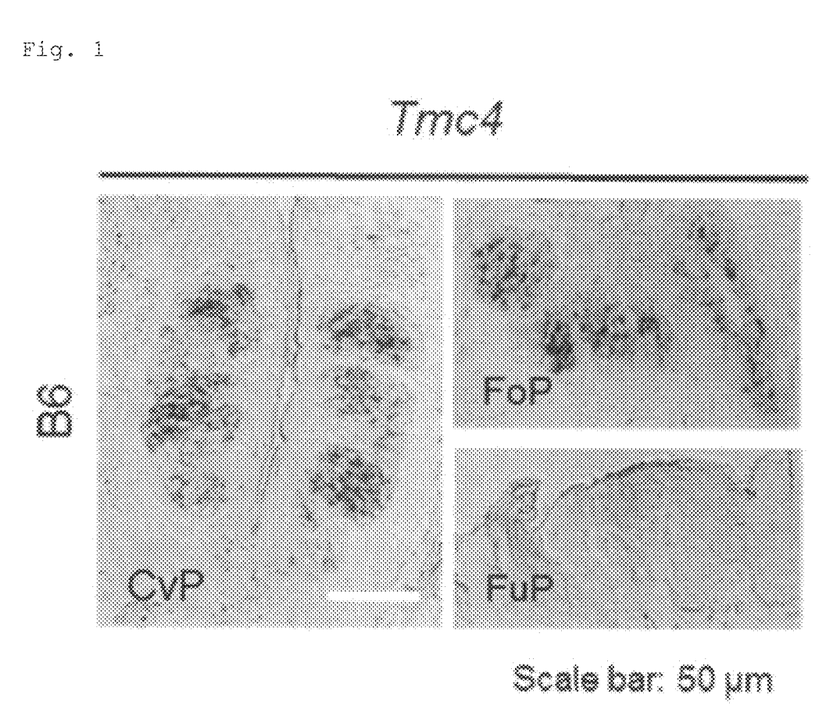
FIG. 1 illustrates stained images obtained by in situ hybridization. CvP: circumvallate papillae, FoP: foliate papillae, FuP: fungiform papillae, scale bar: 50 μm

Results are illustrated in FIG. 1. It was revealed that TMC4 is strongly locally present specifically to the taste buds of the circumvallate papillae (CvP) and foliate papillae (FoP).

[Example 2] Electrophysiological Properties of TMC4

In order to check electrophysiological properties of TMC4, a whole cell patch clamp assay (whole cell recording) was performed using HEK293T cells expressing TMC4.
<Method>
Plasmid and Expressed Protein In order to express mouse TMC4 (mTMC4) in HEK293T cells, a plasmid vector pIRES2-AcGFP1 (Clontech Laboratories, Inc.) having a CMV promoter was used. An expression construct in which mTMC4 (sequence of Accession No. NM_181820.2 cloned from cDNA derived from mouse circumvallate papillae epithelium) was inserted between restriction enzyme EcoR1 site and Not1 site of pIRES2-AcGFP1 was transfected at a ratio of 1 µg/35 mm dish. As a transfection reagent, Lipofectamine™ LTX Reagent with PLUS & Reagent™ (Thermo Fisher Scientific K.K.) was used. Besides, for fluorescent indication, 0.1 µg/35 mm of pEGFP-N1 (Clontech Laboratories, Inc.) was simultaneously transfected.

The transfected cells were seeded in an 18-mm round glass vessel (Matsunami Glass Ind., Ltd.), and cultured again in an incubator (37° C., $CO_2$ concentration: 5% by volume). All experiments were performed within 24 to 36 hours after the transfection to HEK293T cells.

Patch Clamp Method (Patch-Clamp Recording)

In the whole cell patch clamp recording using the HEK293T cells, Axopatch 200B (Molecular Devices, LLC.) was used as an amplifier, and digital data was obtained from Digidata 1550 (Axon Instruments, Union City, Calif., USA). The obtained data was analyzed using software pCLAMP 10.2 (Axon Instruments).

GD-1.5 glass capillary with a filament (NARISHIGE Group) was processed using a micropipette puller P-97/IVF (Sutter Instrument Company) to produce a glass electrode. Its electrode resistance was adjusted to 3-5 MΩ.

The measurement was performed with the membrane potential of mTMC4-expressing cells fixed at −60 mV with extracellular fluids successively perfused. A step pulse (400 ms) from −100 mV to +100 mV at intervals of 10 mV was applied to each extracellular fluid to create an I-V curve, and thus, voltage-current characteristics of mTMC4 obtained with different extracellular fluids were measured. Besides, when an extracellular fluid was instantaneously replaced, the fluid was replaced by perfusion using MicroFil CMF28GxxL (WPI) with ramp waves of ±100 mV applied for 300 ms every 5 seconds to the cells fixed at a voltage of −60 mV. All the measurement was performed at 25° C.

The composition of an intracellular fluid (pipette solution) used in the patch clamp method is shown in Table 1, and the compositions of the extracellular fluids (bath solutions) are shown in Table 2. It is noted that compositions of extracellular fluids used in Example 4 are also shown in Table 2.

The intracellular fluid (pipette solution) was adjusted to pH 7.4 by using N-methyl-D-glucamine (NMDG). Each intracellular fluid was adjusted to have an osmotic pressure of about 270 mosmol/kg.

The extracellular fluids (bath solutions) were adjusted to pH 7.4 by using NMDG-OH. The extracellular fluids were adjusted to have an osmotic pressure of about 290 mosmol/kg.

TABLE 1

| substance(conc: mM) | Pipette solution NMDG-Cl |
|---|---|
| NMDG-Cl | 134 |
| BAPTA | 5 |
| HEPES | 10 |

NMDG-Cl: N-methyl-d-glucamine chloride
BAPTA: O,O'-Bis(2-aminophenyl)ethyleneglycol-N,N,N',N'-tetraacetic acid, tetrapotassium salt, hydrated.
HEPES: 4-(2-hydroxyethyl)-1-piperazineethanesulfonic acid

TABLE 2

| Substance (mM) | Name of bath solution | | | | | | | |
|---|---|---|---|---|---|---|---|---|
| | NaCl (Vehicle) | ½Cr | ¼Cr | Na-gluconate | NPPB | Arg-HCl | Sucrose | Maltose |
| NaCl | 134 | 67 | 34 | — | 134 | 134 | 134 | 134 |
| Na-gluconate | — | 67 | 100 | 134 | — | — | — | — |
| KCl | 2.9 | 2.9 | 2.9 | 2.9 | 2.9 | 2.9 | 2.9 | 2.9 |
| HEPES | 10 | 10 | 10 | 10 | 10 | 10 | 10 | 10 |
| D-Glucose | 15 | 15 | 15 | 15 | 15 | 15 | 15 | 15 |
| $MgCl_2$ | 1.2 | 1.2 | 1.2 | 1.2 | 1.2 | 1.2 | 1.2 | 1.2 |
| $CaCl_2$ | 2.1 | 2.1 | 2.1 | 2.1 | 2.1 | 2.1 | 2.1 | 2.1 |
| NPPB | — | — | — | — | 0.1 | — | — | — |
| Arg-HCl | — | — | — | — | — | 0.1 | — | — |
| Sucrose | — | — | — | — | — | — | 0.1 | — |
| Maltose | — | — | — | — | — | — | — | 0.1 |

NMDG-Cl: N-methyl-d-glucamine chloride
HEPES: 4-(2-hydroxyethyl)-1-piperazineethanesulic acid
NPPB: 5-Nitro-2-(3-phenylpropylamino) benzoic acid <Results>

Figure 2:
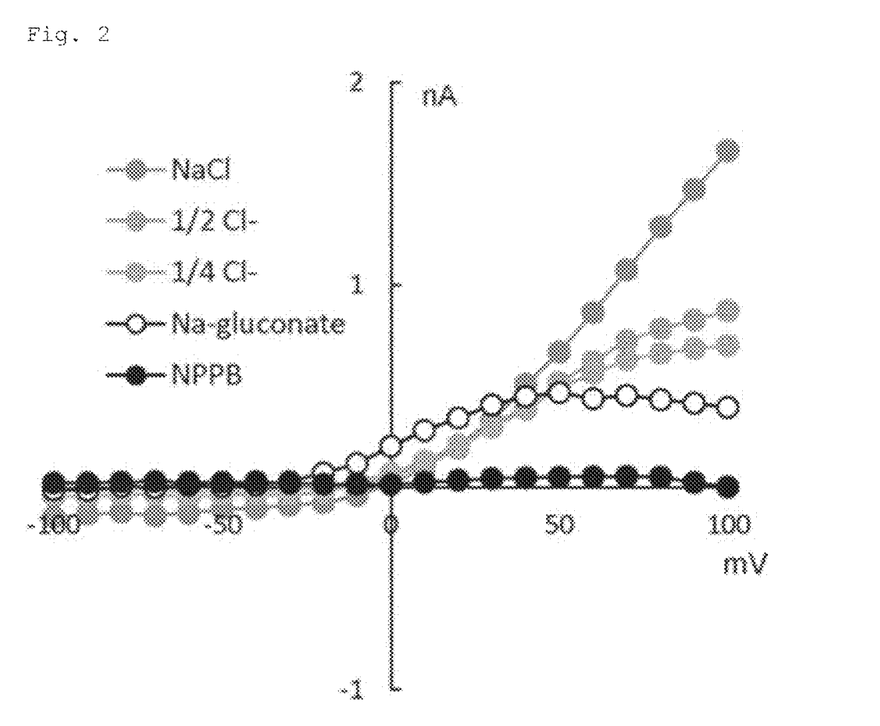
FIG. 2 illustrates results of a whole cell patch clamp assay.

Results are illustrated in FIG. 2.

NaCl (134 mM) of the extracellular fluid was replaced with Na-gluconate (sodium gluconate) in a stepwise manner, and thus, the extracellular fluid was changed successively to 100 mM Cl⁻ (NaCl 100 mM, Na-gluconate 34 mM), 50 mM Cl⁻ (NaCl 50 mM, Na-gluconate 84 mM) and 134 mM Na-gluconate (0 mM Cl⁻). Thus, the magnitude of an outward Cl⁻ current was reduced in accordance with the reduction of the Cl⁻ concentration. When Cl⁻ was completely replaced with gluconate, the outward current did not disappear. When 100 µM NPPB, that is, a Cl⁻ channel inhibitor, was added to the 134 mM NaCl buffer, however, the current completely disappeared. This suggests a possibility that TMC4 may be an outward-rectifying Cl⁻ channel having a pore size allowing a large molecule like gluconate to pass therethrough.

[Example 3] TMC4 Gene Knockout Mouse

In order to observe the influence of TMC4 on salty taste receiving behavior, a TMC4 gene knockout mouse (KO) was produced to perform a lick analysis experiment (brief access test).

<Method>

TMC4 KO Mouse

Animal experimentation was approved, and was performed in compliance with an animal experimentation manual.

A TMC4 KO mouse was created with a C57BL/6J mouse used as a genetic background by TALEN method (Institute of Immunology Co., Ltd.). A founder mouse of a TMC4 KO mouse was backcrossed, and a DNA extracted from the tail of the mouse was then used to perform sequence analysis of TMC4 genome sequence, and thus, it was checked whether or not there was a frameshift. Littermates WT mice (+/+) and KO mice (−/−), both males, 7-week-old or older, produced by crossing heterozygous mice (+/−) among TMC4 KO mice were used. The mice were fed with normal diet (Lab MR Breeder, Nosan Corporation), and were raised at a constant temperature of 22±1° C. with light/dark cycles of 12 hours (light on at 8:00 a.m.).

Lick Analysis Experiment (Brief Access Test)

The lick analysis experiment is a method in which a taste solution is presented to an experimental animal for a short time to count the number of times of the animal licking a faucet (licking number), and is a test by which taste recognition (via the brain) alone excluding post-ingestive effects can be measured.

TMC4 KO mice (−/−, 7-week-old or older, n=7) and their wild-type littermates (+/+, 7-week-old or older, n=9) were used. The test was performed for comparing the five tastes of sweet taste, umami, bitter taste, sour taste and salty taste with water. The test for sweet taste and umami (tastes ingested palatably at a threshold or higher level) was performed after water deprivation for 4 hours while allowing to free access to feed. On a day of the test for bitter taste, sour taste and salty taste (tastes repellent at a threshold or higher level), the test was performed after water deprivation for 23 hours while allowing to free access to feed. As for salty taste presumed as palatable, a diuretic agent of furosemide was subcutaneously injected in an amount of 50 mg/kg of body weight to each mouse, followed by fasting and water deprivation for 6 hours.

In order to eliminate the influence of fluid restriction on health condition as much as possible, it was checked through measurement that each individual kept 80% or more of its weight at the time of starting the test.

To measure the licking number, licking behavior was recorded using a digital camera (VSK0780; Panasonic Corporation), and based on the recorded images, the licking number for five seconds from the mouse starting to lick the faucet after presenting each taste solution was counted. A ratio of the licking number for the taste substance solution to a licking number for five seconds for ultrapure water after water deprivation (assumed as the licking number at the highest speed) was defined as a lick ratio: (lick ratio)/(average of licking number for ultrapure water after water deprivation).

Responses of WT and KO mice were tested through comparison between groups by two-way ANOVA.

<Results>

Mice acclimated for the test (WT: n=9, KO: n=7, all males, 20-week-old or older) were used. The licking number for 5 seconds was measured after fasting and water deprivation for 4 hours for the tastes generally palatable concentration-dependently (sweet taste and umami), and after water deprivation and free access to feed for 23 hours for the tastes repellent as the concentration increases (bitter taste, sour taste and salty taste). Assuming that the number of licking water after water deprivation for 23 hours is 1, a ratio to this reference was calculated.

As for the taste solutions used in the test, a sucrose (Wako Pure Chemical Industries, Ltd.) solution was used for sweet taste, a mixture solution of sodium glutamate (MSG) (Wako Pure Chemical Industries, Ltd.) and 0.5 mM inosinic acid (IMP) (Wako Pure Chemical Industries, Ltd.) was used for umami, a quinine hydrochloride (Wako Pure Chemical Industries, Ltd.) solution was used for bitter taste, a citric acid (Wako Pure Chemical Industries, Ltd.) solution was used for sour taste, and a NaCl (Kanto Chemical Co., Inc.) solution was used for salty taste.

Figure 3:
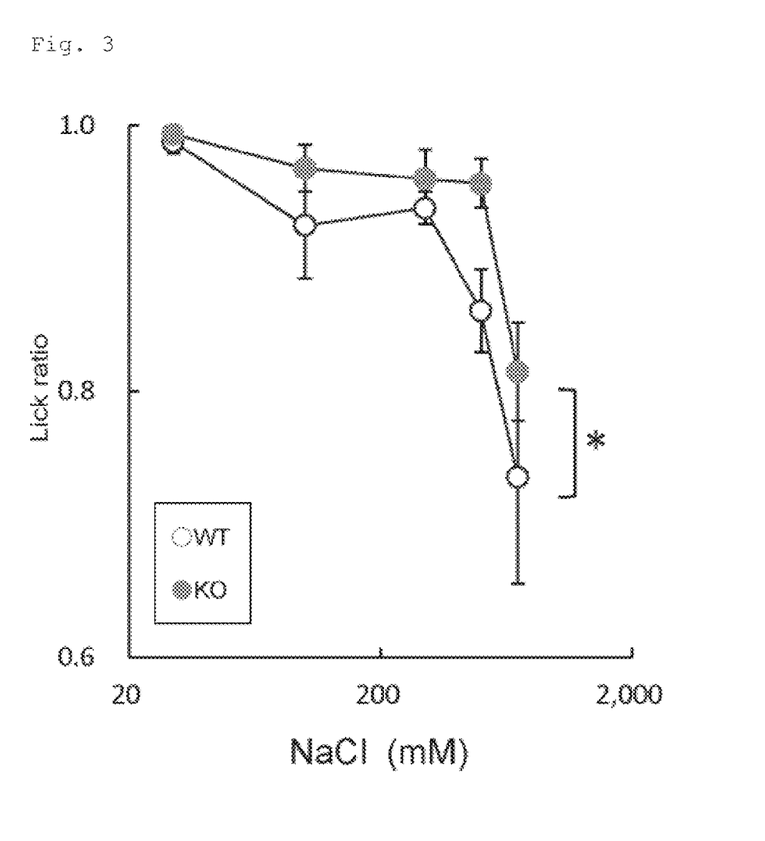
FIG. 3 illustrates results of a brief access test.

Results are illustrated in FIG. 3. When NaCl was used as salty taste of the taste solution, there was a significant difference (significance level: 5%) in the comparison between groups of WT mice and KO mice (two-way ANOVA), and response (sensitivity) to NaCl was lower in the KO mice than in the WT mice. On the other hand, as for the other tastes and the salty taste presumed as palatable, no significant difference was observed between the groups of WT mice and KO mice.

[Example 4] Influence of Known Salty Taste Enhancer on Electrophysiological Properties of TMC4

In order to observe influence of a known salty taste enhancer on TMC4, the whole cell patch clamp assay (whole cell recording) was performed by using HEK293T cells expressing human TMC4 (hTMC4).

<Method>

The whole cell patch clamp assay was performed in the same manner as in Example 2 except for the following:

1) HEK293T cells expressing human TMC4 (hTMC4) were used; and 2) a 134 mM NaCl solution was used as a vehicle solution, an extracellular fluid obtained by adding 100 μM arginine hydrochloride (Arg-HCl) as a salty taste enhancer to the vehicle solution, and an extracellular fluid (control not enhancing salty taste) obtained by adding 100 μM sucrose or maltose to the vehicle solution were used. A Cl$^-$ current flowing via TMC4 was compared.

As for the hTMC4, a clone of Accession No. BC025323 was purchased from Dharmacon, and inserted between restriction enzyme EcoR1 site and Not1 site of the plasmid pIRES2-AcGFP1 to create an expression construct in the same manner as that for the mTMC4.

<Results>

Figure 4:
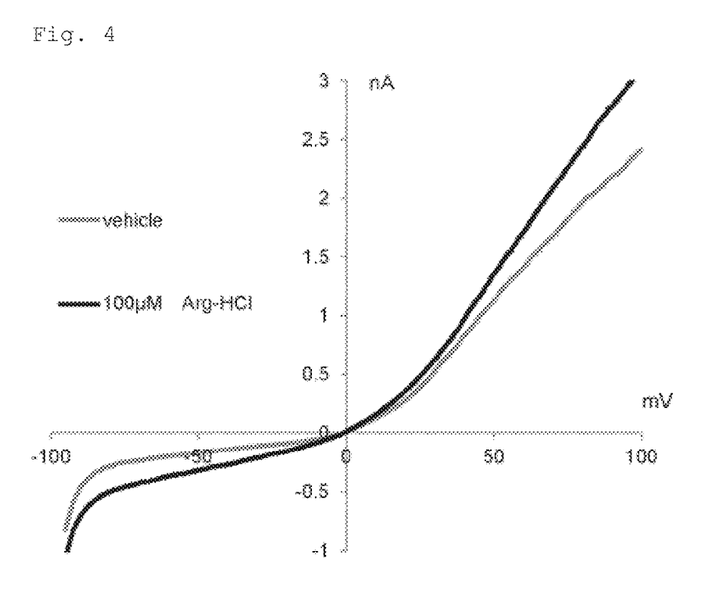
FIG. 4 illustrates an example of a result of measurement of salty taste enhancing effect using a salty taste enhancer, arginine hydrochloride (Arg-HCl).
Figure 5:
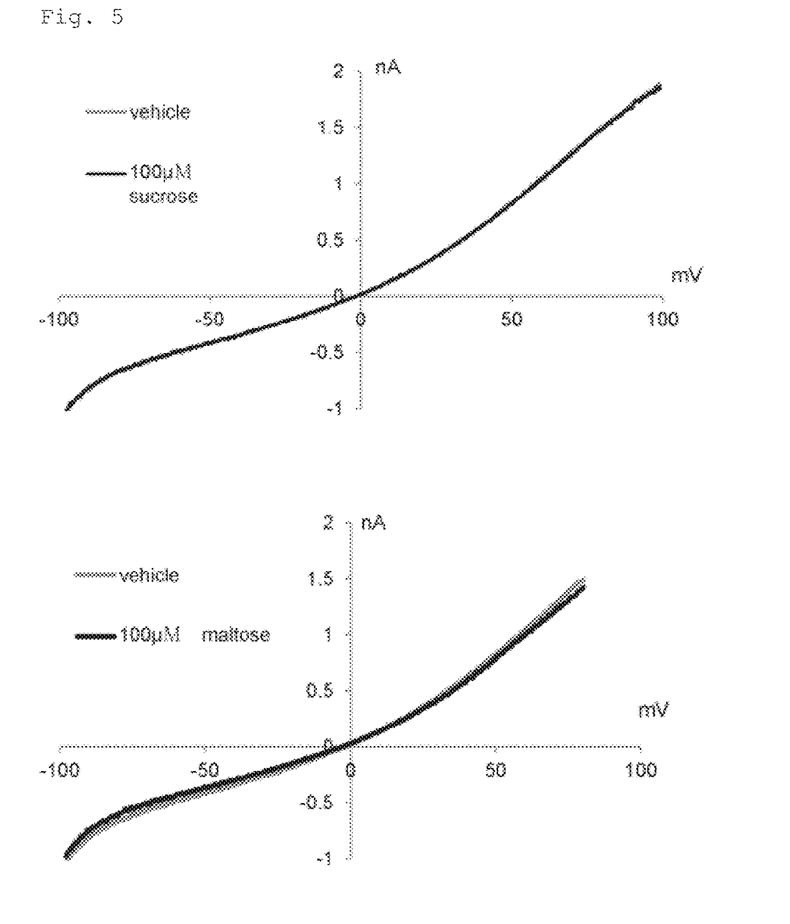
FIG. 5 illustrates an example of a result of the measurement of the salty taste enhancing effect using sucrose and maltose not affecting salty taste.

Results are illustrated in FIGS. 4 and 5.

When 100 μM arginine hydrochloride used as the salty taste enhancer was added to the vehicle solution, the Cl$^-$ current flowing through the same cells was increased. On the other hand, when 100 μM sucrose or maltose, neither of which had the salty taste enhancing effect, was added, the Cl$^-$ current flowing through the same cells did not change. This reveals that a Cl$^-$ current flowing through cells expressing TMC4 is activated by arginine hydrochloride, that is, a salty taste enhancer.

Accordingly, when a substance that increases a Cl-current is searched by the whole cell patch clamp assay using HEK293T cells expressing TMC4, a candidate of a salty taste enhancer can be found.

The invention claimed is:

1. A method for screening for an active ingredient of a salty taste enhancer, comprising the steps of:
   (i) determining whether or not a test substance is a compound capable of upregulating functional expression of TMC4 gene or TMC4 protein; and
   (ii) selecting a test substance determined in step (i) to be the compound capable of upregulating functional expression of TMC4 gene or TMC4 protein, as the active ingredient of a salty taste enhancer.

* * * * *